United States Patent [19]

Dursch

[11] 3,940,483

[45] Feb. 24, 1976

[54] ANTIBIOTIC COMPOSITIONS AND METHOD
[75] Inventor: Friedrich Dursch, Hopewell, N.J.
[73] Assignee: E. R. Squibb & Sons, Inc., Princeton, N.J.
[22] Filed: Oct. 18, 1971
[21] Appl. No.: 190,325

Related U.S. Application Data
[63] Continuation-in-part of Ser. No. 113,105, Feb. 5, 1971, abandoned.

[52] U.S. Cl. ................ 424/246; 424/227; 424/271
[51] Int. Cl.$^2$ ................................ A61K 31/545
[58] Field of Search ................................ 424/246

[56] References Cited
UNITED STATES PATENTS
3,136,691  6/1964  Nordstrom et al. .............. 424/43
3,485,819  12/1969  Weisenborn et al. ............. 424/246

FOREIGN PATENTS OR APPLICATIONS
2,035,118  12/1970  France

OTHER PUBLICATIONS
Chemical Abstracts 60:1548c (1964).
Chemical Abstracts 46:9807c.

Primary Examiner—Jerome D. Goldberg
Assistant Examiner—Allen J. Robinson
Attorney, Agent, or Firm—Lawrence S. Levinson; Merle J. Smith; Donald J. Barrack

[57] ABSTRACT

Dry solid antibiotic compositions are provided comprising a solid acidic, basic or amphoteric antibiotic and a suitable solid basic or acidic additive, for reconstitution as injectables upon addition of water.

A method is also provided for formulating injectable antibiotics.

4 Claims, No Drawings

ANTIBIOTIC COMPOSITIONS AND METHOD

This application is a continuation in part of application Ser. No. 113,105 filed Feb. 5, 1971 now abandoned.

Antibiotics of limited water solubility are currently formulated for parenteral application either as aqueous suspensions, or by preparing water soluble derivatives (e.g., salts, esters or complexes) of the parent compound, which upon administration are either in equilibrium with the parent compound, or which are transformed back into the parent compound in the patient's system. Inherent in these practices are several problems. Use of solids in suspension severely limits the mode of parenteral administration. Furthermore, preparation of pharmaceutically acceptable solid derivatives is frequently accompanied by significant yield losses. Moreover, some otherwise desirable derivatives cannot be isolated in suitable form altogether (e.g., in pure crystalline or other stable forms).

A new way has now been found which circumvents the problems inherent in pre-forming water soluble derivatives of antibiotics for parenteral administration in certain cases. Solid antibiotics of limited water solubility which are either acidic, basic, or amphoteric in nature, are blended as dry powders with suitable solid additives. Upon addition of water to such dry mixtures, physiologically acceptable solutions of water soluble salts of the antibiotic are formed in situ and can be administered without delay. Problems of storage stability or preparation yield losses are completely eliminated in this way. Combinations of antibiotics with desirable counter ions can often be selected that heretofore would be excluded because of their physical properties or their limited storage stability.

Accordingly, the present invention relates to dry solid antibiotic compositions comprising a solid acidic, basic or amphoteric antibiotic and a suitable solid basic or acidic additive, for reconstitution as injectables upon addition of water. Furthermore, a method is provided for formulating injectable antibiotics, which comprises blending solid acidic, basic, or amphoteric antibiotics with suitable solid basic or acidic additives to provide stable dry mixtures and adding sufficient sterile water thereto to form clear solutions suitable for injection.

Examples of amphoteric antibiotics of water solubility insufficient for direct formulation as injectables and useful in the present invention include, but are not limited to penicillins like α-aminobenzylpenicillin (ampicillin) and α-amino-2,5-dihydrobenzylpenicillin (epicillin), cephalosporins like α-aminobenzyl-3-desacetoxycephalosporin (cephalexin) and α-amino-2,5-dihydrobenzl-3-desacetoxycephalosporin (cephradine), tetracycline and oxytetracyline. Examples of suitable acidic antibiotics, useful in the present invention, include, but are not limited to phenoxymethyl penicillin (penicillin V) and substituted 4-isoxazolyl penicillins (e.g., oxacillin, cloxacillin, dicloxacillin). Erythromycin is an example of a basic antibiotic suitable for formulation according to the present invention.

Suitable additives for acidic antibiotics are usually of basic nature, while additives for basic antibiotics are commonly acidic. Suitable additives for amphoteric antibiotics may be of either acidic or basic character. These additives are substantially non-toxic and non-irritating in nature when used according to the present invention.

Examples of suitable basic additives useful in the present invention include, but are not limited to alkali metal carbonates, for example sodium carbonate, alkali metal bicarbonates, for example sodium bicarbonate, ammonium carbamate, alkali metal or ammonium phosphates, for example sodium or potassium phosphate, organic amines like N-methylglucamine, tris(hydroxymethyl)aminomethane and the like.

Examples of suitable solid acidic additives useful in the present invention include, but are not limited to, alkali metal hydrogen sulfates, for example sodium or potassium hydrogen sulfate, and organic acids like citric acid, tartaric acid or maleic acid.

The selected solid additive is usually employed in an amount just sufficient to assure complete dissolution of the antibiotic upon addition of a small volume of water. This amount may well be less than the stoichiometric quantity required for complete conversion to a salt. Herein lies another advantage of the present invention over the use of pre-formed salts; frequently, less extreme conditions of acidity or basicity are required for complete dissolution and superior stability of such solutions can be expected. For example, 95 mole-% of sodium carbonate is sufficient to dissolve ampicillin at pH 8.3, whereas an aqueous solution of preformed sodium ampicillin shows about pH 9.5.

The preferred antibiotic composition of the invention comprises cephradine in combination with sodium carbonate.

In forming the injectable solution, sufficient sterile water is added to the solid mixture to provide a concentration of active antibiotic of about 50 to 500 milligrams per milliliter of water, preferably of above 200 milligrams per milliliter of water to 500 milligrams per milliliter of water.

The injectables formulated in accordance with the invention can be employed in the same manner and for the same utility as the parent antibiotics.

The following examples further illustrate the invention. In each example, a solid antibiotic of limited water solubility is blended with a solid additive. The mixtures are then combined with small amounts of water and are subsequently gently shaken for about one minute. Clear solutions are obtained in all cases, indicating complete dissolution of the antibiotic and suitability of the mixture as an injectable formulation.

EXAMPLE 1

An intimate blend is prepared from 600 milligrams of penicillin V as the free acid with 265 milligrams of tris(hydroxymethyl)aminomethane. Addition of 1.5 ml of sterile water results in the formation of a clear solution of pH 7.9, suitable for injection.

EXAMPLE 2

A blend is prepared from 500 milligrams of dicloxacillin and 255 milligrams of N-methyl-glucamine. A clear solution of pH 8.6 is formed upon addition of 2.5 milliliters of sterile water, suitable for injection.

EXAMPLE 3

A dry mixture of 400 milligrams of epicillin and of 150 milligrams of sodium hydrogen sulfate is reconstituted with 10 milliliters of sterile water to give a clear solution, suitable for parenteral application.

EXAMPLE 4

An intimate blend is prepared from 400 milligrams of ampicillin trihydrate and of 100 milligrams of anhydrous sodium carbonate. The mixture is shaken gently with 12 milliliters of sterile water to give a clear solution of pH 8.3, suitable for injection.

EXAMPLE 5

A dry mixture of 600 milligrams of α-amino-2,5-dihydrobenzyl-3-desacetoxycephalosporin (cephradine) and of 450 milligrams of trisodium phosphate dodecahydrate is reconstituted with 10 milliliters of sterile water to give a clear injectable solution of pH 8.5.

EXAMPLE 6

An intimate blend is prepared from 500 milligrams tetracycline base with 340 milligrams of anhydrous potassium carbonate. Addition of 2.5 milliliters of sterile water results in formation of an injectable solution of pH 9.7.

EXAMPLE 7

A dry mixture of 250 milligrams of erythromycin base with 110 milligrams of maleic acid is reconstituted with 1.25 milliliters of sterile water. An injectable solution of pH 2.0 is obtained.

EXAMPLE 8

A dry mixture of 0.56 gram α-amino-2,5-dihydrobenzyl-3-desacetoxycephalosporin (cephradine) and of 0.15 gram anhydrous sodium carbonate is reconstituted with 2.5 milliliters of sterile water. An injectable solution of pH 8.5 is obtained.

EXAMPLE 9

A dry mixture of 0.56 gram cephalexin and of 0.17 gram anhydrous sodium carbonate is reconstituted with 3 milliliters of sterile water. An injectable solution of pH 8.4 is obtained.

What is claimed is:

1. A dry solid antibiotic composition suitable for reconstitution as an injectable upon addition of water which comprises cephradine and sodium carbonate, the sodium carbonate being present in an amount sufficient to assure complete dissolution of the cephradine in an amount of sterile water which provides a concentration of active cephradine of from about 50 to 500 milligrams per milliliter of water.

2. A composition in accordance with claim 1 wherein the sodium carbonate is present in an amount sufficient to assure complete dissolution of cephradine in an amount of sterile water which provides a concentration of active cephradine of from above 200 milligrams per milliliter of water to 500 milligrams per milliliter of water.

3. A method for formulating cephradine in injectable form which comprises blending cephradine with sodium carbonate to provide a stable dry mixture and adding sufficient sterile water thereto to provide a concentration of active cephradine of from about 50 to 500 milligrams per milliliter of water, wherein the sodium carbonate is added in an amount sufficient to assure complete dissolution of the cephradine.

4. A method in accordance with claim 3 wherein sufficient sterile water is added to the stable dry mixture to provide a concentration of active cephradine of from above 200 milligrams per milliliter of water to 500 milligrams per milliliter of water.

* * * * *